US00PP18640P2

(12) United States Plant Patent
Cripps et al.

(10) Patent No.: US PP18,640 P2
(45) Date of Patent: Mar. 25, 2008

(54) APPLE TREE NAMED 'WESTERN DAWN'

(50) Latin Name: *Malus domestica*
Varietal Denomination: Western Dawn

(75) Inventors: John E. L. Cripps, South Perth (AU); Eleanor Melvin-Carter, South Perth (AU)

(73) Assignee: Western Australian Agriculture Authority, Western Australia (AU)

( * ) Notice: Subject to any disclaimer, the term of this patent is extended or adjusted under 35 U.S.C. 154(b) by 0 days.

(21) Appl. No.: 11/444,904

(22) Filed: May 31, 2006

Related U.S. Application Data

(60) Provisional application No. 60/686,556, filed on Jun. 1, 2005.

(51) Int. Cl.
*A01H 5/00* (2006.01)

(52) U.S. Cl. ..... Plt./161

(58) Field of Classification Search ..... Plt./161, Plt./172

See application file for complete search history.

*Primary Examiner*—Kent Bell
(74) *Attorney, Agent, or Firm*—Stratton Ballew PLLC

(57) ABSTRACT

'Western Dawn' is a new and distinct cultivar of *Malus domestica* Mill. notable for its pinkish-red blush skin color, its late maturity, and its marked resistance to oxidative browning.

6 Drawing Sheets

Latin name of the genus and species of the plant claimed: *Malus domestica* (Borkh.).
Variety denomination: 'Western Dawn'.

BACKGROUND OF THE INVENTION

'Western Dawn' originated as a seedling produced from a controlled cross performed in a sexual breeding program conducted by the State of Western Australia at Stoneville Research Station, Western Australia in the fall of 1976. It was bred using conventional breeding techniques. 'Western Dawn' is a cross between female parent 'Lady Williams' (not patented), a chance seedling originating in Western Australia, and male parent 'Golden Delicious' (not patented), and is a sister of 'Cripps Pink' (Pink Lady®, U.S. Plant Pat. No. 7,880), 'Cripps-Two' (Sundowner®, U.S. Plant Pat. No. 8,477) and 'Big Time' (not patented). 'Western Dawn' was first asexually propagated, by grafting onto rootstocks, at Stoneville Research Station in 1982 for testing purposes, and has been shown to remain true to type over successive generations.

'Western Dawn' is distinguishable from its parents by its maturity date and skin color. 'Western Dawn' matures earlier than 'Lady Williams' (late versus very late) and has a red-pink skin color as compared to the yellow skin of 'Golden Delicious'.

Western Dawn was selected on fruit quality characteristics, including:

- excellent eating qualities
- an appealing bright pinkish red color, which stands out from other varieties
- bright creamy white flesh, which does not oxidize after cutting.

BRIEF DESCRIPTION OF THE PHOTOGRAPHS

Figure 1:
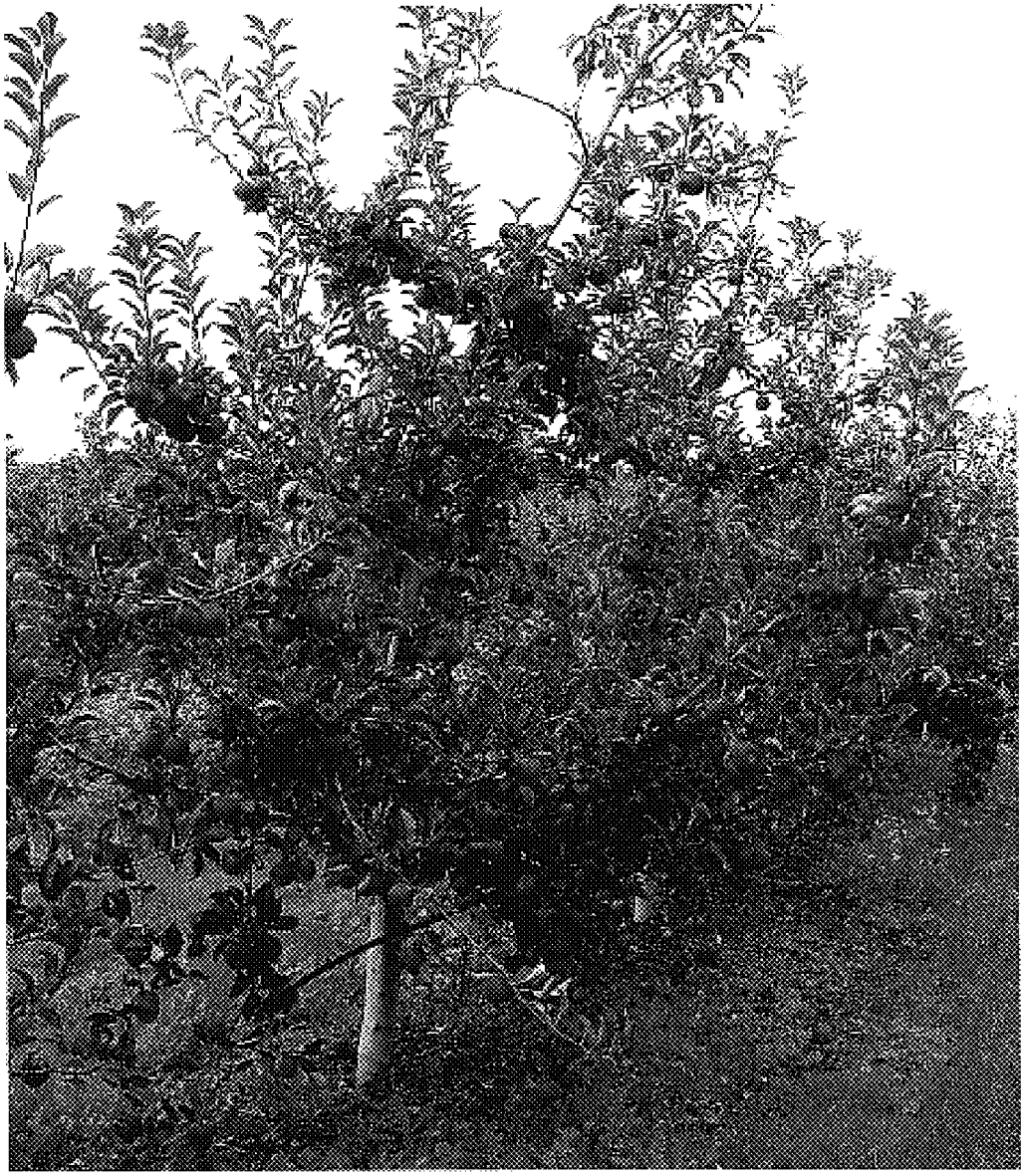

FIG. 1 Tree of the apple variety 'Western Dawn' taken just prior to harvest

Figure 2:
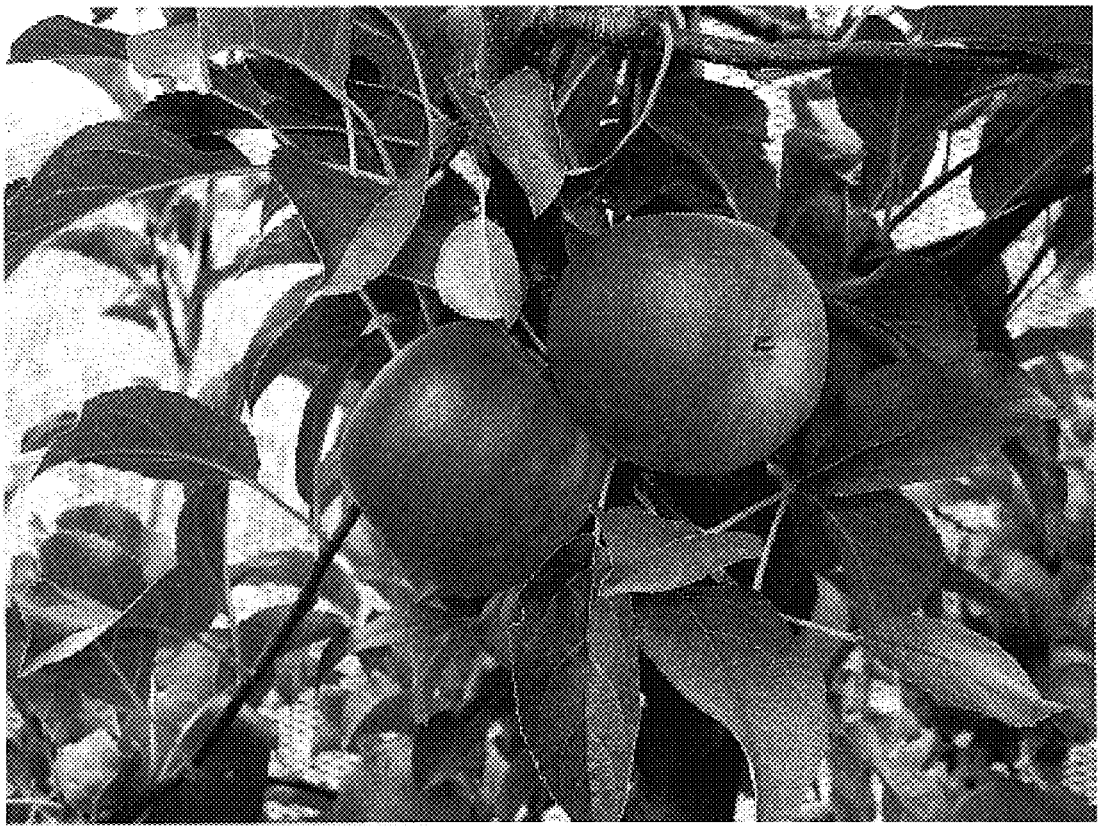

FIG. 2 Fruit of the apple variety 'Western Dawn' showing development on the tree just prior to harvest (2 May 2006)

Figure 3:
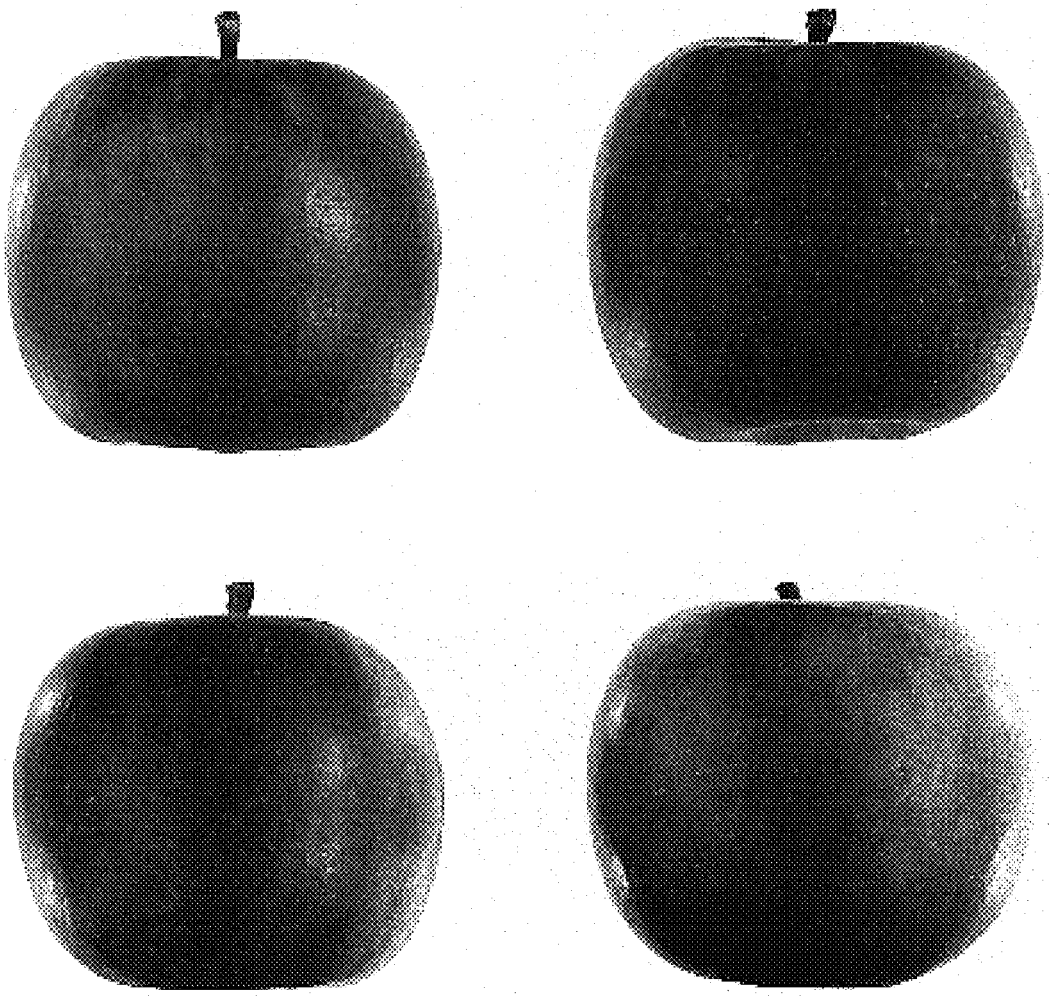

FIG. 3 Fruit of the apple variety 'Western Dawn' showing side view

Figure 4:
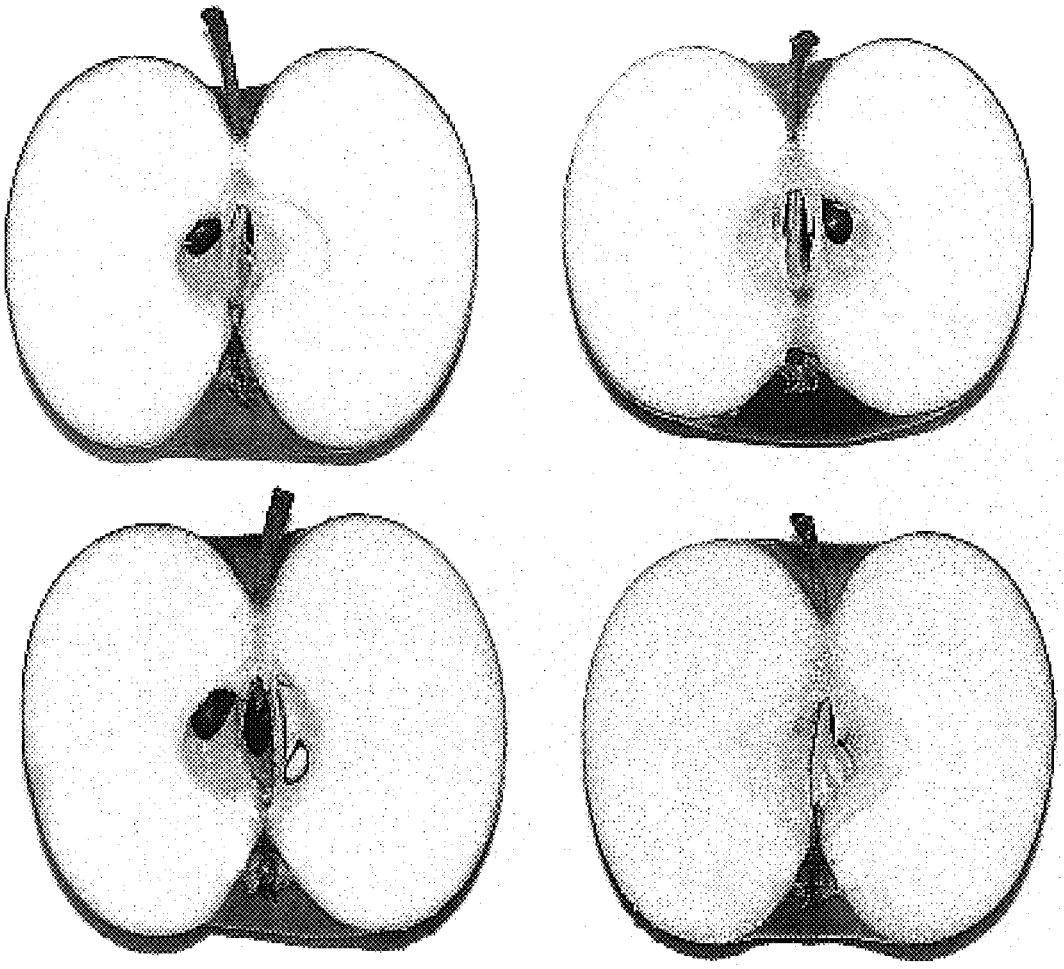
Figure 5:
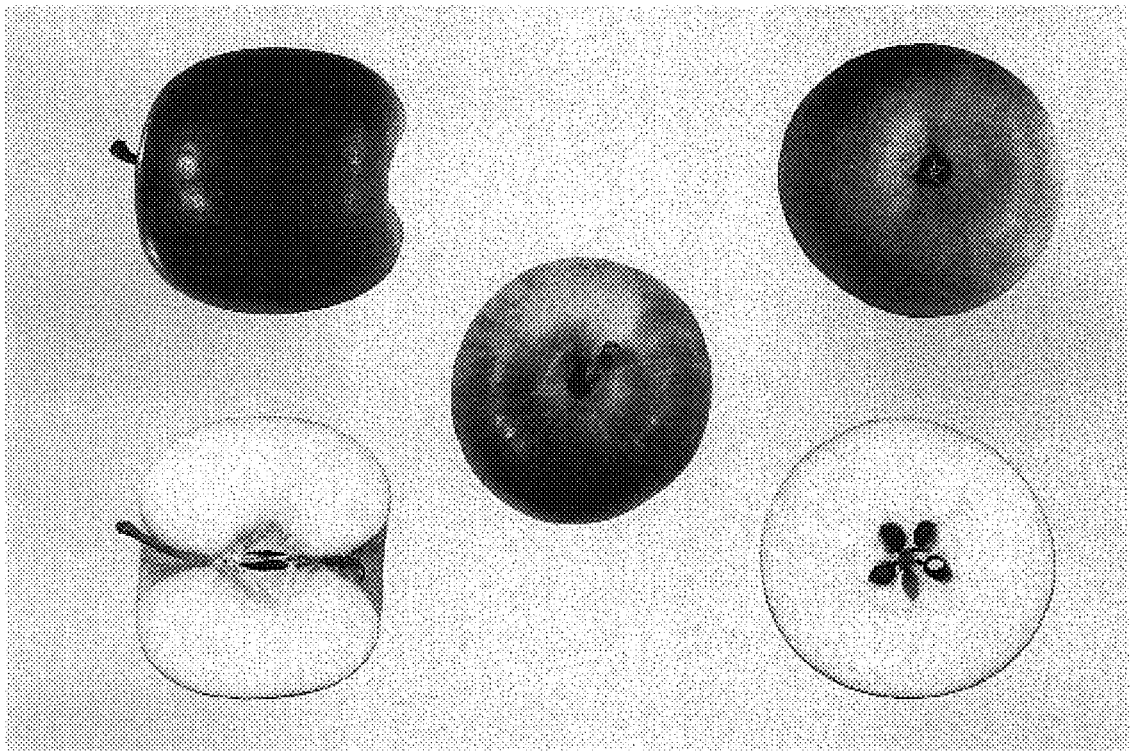
Figure 6:
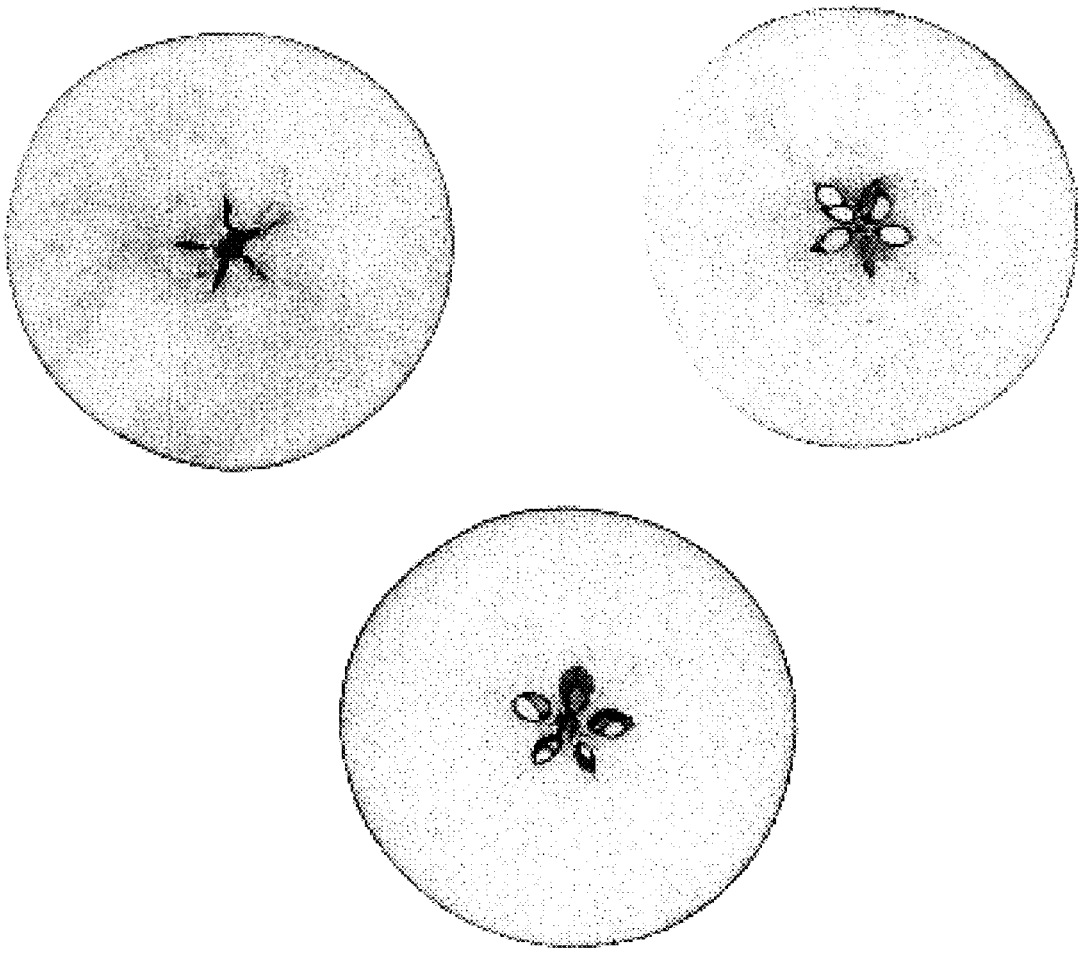

FIG. 4 Fruit of the apple variety 'Western Dawn' showing vertical cross-section FIG. 5 Fruit of the apple variety 'Western Dawn' showing side view, calyx, view, stalk end view, horizontal cross-section and vertical cross-section FIG. 6 Oxidation (browning) of 'Western Dawn' (bottom), 'Cripps Pink' (Pink Lady®) (top right) and 'Red Fuji' (top left) after 30 minutes.

DETAILED BOTANICAL DESCRIPTION

The following detailed botanical description is based on observations of 4 year old trees made during the 2005/2006 growing season at Manjimup Horticultural Research Institute, Manjimup, Western Australia. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Tree:
   *Vigor.*—Strong.
   *Type.*—Ramified.
   *Habit.*—Upright.
   *Size.*—Height, 3.0 m; diameter, 1.9 m.
   *Trunk.*—Diameter 4.8 cm at 30 cm above ground level; bark texture smooth (observed on young trees; may change as trees age); grey 201D.

*Branches.*—Length 87.6 cm; diameter 12.5 mm; crotch angle 70° to 100°; grey-brown 199B (branches measured were 2 years old, directly off the central leader and between 1 and 1.5 m above the ground).

*Winter hardiness.*—Not known.

*Chilling requirement.*—Medium, approximately 400 to 500 hours below 7.2 degrees Celsius.

2. Dormant one year old shoot:

*Pubescence on upper half of shoot.*—Medium.

*Size.*—Diameter 6.2 mm (measured at the center of the shoot); length 54.9 cm.

*Color.*—greyed-orange 165A.

*Internode length.*—Short, 20.1 mm.

*Number of lenticels.*—Medium.

3. Flowers:

*Bud.*—Quantity per spur 10.9 (spurs measured were 5 to 10 cm long as trees of this age have not produced well defined spur wood); shape round to conical; length 18.0 mm (flower buds measured at balloon stage just prior to opening); diameter 12.7 mm (flower buds measured at balloon stage just prior to opening).

*Flower color (balloon stage).*—Red-purple 64C (observation made on second or third flower bud when the terminal (King) flower is opening).

*Size.*—Diameter large, 49.6 mm (open flowers with petals pressed into the horizontal position measured); depth 14.8 mm; Quantity per cluster 6.3.

*Petals.*—Quantity per flower 5; Relative position of petal margins touching; length 23.7 mm; width 16.5 mm; apex shape rounded; base shape rounded; upper surface purple 76D (measured when flowers fully open); lower surface purple 75A (measured when flowers fully open).

*Sepals.*—Quantity per flower 5; shape long narrow triangular, apex narrow pointed; length 10.7 mm; green 138C.

*Pedicel.*—Length 23.6 mm; diameter 1.4 mm; color grey-brown 199A.

*Pistil.*—Length 15.8 mm.

*Anthers.*—Quantity per flower avg. 18.6; length 2.0 mm; pollen color yellow 12D.

*Stigma.*—Color light green.

*Style.*—Length 11.1 mm; Color light green/yellow.

*Ovary.*—Size 4.8 mm.

*Bloom period.*—First bloom 24 October, full bloom 11 November (2005/2006 growing season at Manjimup Horticultural Research Institute).

4. Leaf:

*Attitude in relation to shoot.*—Upwards.

5. Leaf blade:

*Length.*—Short to medium 85.3 mm.

*Width.*—Narrow 47.5 mm.

*Length-width ratio.*—Large.

*Margin.*—Biserrate.

*Shape.*—Oval; base rounded; tip apiculate.

*Color.*—Upper surface yellow-green 147A; lower surface yellow green 148B.

6. Petiole: Length medium 35.0 mm; diameter medium 2.0 to 2.5 mm; color yellow-green 147C.

7. Fruit:

*Size.*—Mass 165.3 g; diameter 70.7 mm; height 63.4 mm (average of 50 fruit harvested randomly).

*Ratio of height to width.*—Small to medium, avg. 0.9.

*General shape in profile.*—Cylindrical.

*Position of maximum diameter.*—Center.

*Ribbing.*—Weak.

*Crowning at calyx end.*—Weak.

*Aperture of eye.*—Open.

*Size of eye.*—Medium, 7.9 mm.

*Depth of eye basin.*—Medium, 9.5 mm.

*Width of eye basin.*—Broad, 37.4 mm.

*Stalk.*—Diameter 2.1 mm (measured at the mid-point of the stalk); Length 28.1 mm; color greyed-orange 165B.

*Depth of stalk cavity.*—Medium, 16.2 mm.

*Width of stalk cavity.*—Medium, 34.9 mm.

*Size of lenticels.*—Medium, diameter 0.53 mm.

*Bloom of skin.*—Weak.

*Greasiness of skin.*—Moderate; greasy when overmature.

*Ground color of skin.*—Green-yellow 1D.

*Over color of skin.*—Red 47A.

*Amount of over color.*—Medium to large; 60% to 90% of the skin surface.

*Intensity of over color.*—Medium.

*Pattern of over color.*—Only solid flush (very weakly defined striping on a few fruit).

*Flesh.*—Texture medium to firm, 8.1 kg/cm on 1 May 2006 at Manjimup Horticultural Research Institute; juicy, 66% juice from fruit sampled on 3 May 2006; color light cream 155B.

*Seeds.*—Quantity per fruit 8 to 10; color greyed-orange 166A.

*Quantity per cluster.*—Fruit thinned to between 1 and 2 per cluster.

*Oxidation of the flesh after 30 minutes.*—Absent to weak.

*Yield.*—Moderate to heavy; mature free standing central leader trees at Manjimup produced an estimated 40 tonnes per hectare.

Use: Fresh market and minimum processing.

Resistance to known diseases: Pest and disease resistance in Manjimup is similar to 'Cripps Pink' and 'Cripps-Two'.

Disorders: The fruit is not prone to sunburn, surface cracking, bitter pit or internal disorders under Western Australian conditions. Some fruit drop has been noted within two weeks of harvest and use of a fruit fixer or sticker is advisable. Some russet has been observed in some seasons, for example, when 'Golden Delicious' russets.

Storageability: 'Western Dawn' has moderate storage capacity. It is not suitable for very long-term storage.

It is claimed:

1. We claim a new and distinct apple tree substantially as shown and described herein.

* * * * *